United States Patent
Oda et al.

(10) Patent No.: US 7,399,596 B2
(45) Date of Patent: Jul. 15, 2008

(54) METHOD FOR PREDICTING PREGNANCY-INDUCED HYPERTENSION

(75) Inventors: Hiroshi Oda, Ibaraki (JP); Kosuke Seiki, Ibaraki (JP); Yasuhiko Shiina, Ibaraki (JP); Nobuyuki Sato, Ibaraki (JP); Satoru Takeda, Saitama (JP); Naomi Eguchi, Osaka (JP); Yoshihiro Urade, Kyoto (JP)

(73) Assignees: Maruha Corporation, Tokyo (JP); Osaka Bioscience Institute, Suita-shi (JP)

( * ) Notice: Subject to any disclaimer, the term of this patent is extended or adjusted under 35 U.S.C. 154(b) by 0 days.

(21) Appl. No.: 10/573,072

(22) PCT Filed: Sep. 24, 2004

(86) PCT No.: PCT/JP2004/014455

§ 371 (c)(1),
(2), (4) Date: Mar. 23, 2006

(87) PCT Pub. No.: WO2005/029081

PCT Pub. Date: Mar. 31, 2005

(65) Prior Publication Data

US 2007/0020609 A1 Jan. 25, 2007

(30) Foreign Application Priority Data

Sep. 24, 2003 (JP) .............................. 2003-332084

(51) Int. Cl.
*G01N 33/53* (2006.01)
(52) U.S. Cl. ....................................................... 435/7.1
(58) Field of Classification Search .................. 435/7.1
See application file for complete search history.

(56) References Cited

U.S. PATENT DOCUMENTS

| | | | | |
|---|---|---|---|---|
| 6,461,827 B1 * | 10/2002 | Oda et al. | .................. | 435/7.92 |
| 6,790,635 B1 | 9/2004 | Seiki et al. | | |
| 2003/0190678 A1 | 10/2003 | Mase et al. | | |
| 2004/0038314 A1 | 2/2004 | Oda et al. | | |

FOREIGN PATENT DOCUMENTS

| EP | 099447 | 5/1998 |
|---|---|---|
| EP | 0999447 | 5/1998 |
| EP | 1111387 | 6/2001 |
| JP | 2001-215226 | 8/2001 |
| JP | 2004-220354 | 8/2001 |

OTHER PUBLICATIONS

Manya et al, Comparative study of the asparagine-linked sugar chains of human lipocalin-type prostaglandin d syntase purified from urine and amniotic fluid, and recombinantly expressed in chinese hamster ovary cells, 2000, J Biochem, vol. 127, pp. 1001-1011.*
Eguchi et al, Expression of lipocalin-type prostaglandin D synthase (B-trace) in human heart and its accumulation in the coronary circulation of angina patients, 1997, PNAS, vol. 94 14689-94.*
Hirawa et al, Lipocalin-type prostaglandin D synthase in essential hypertension, 2002, Hypertension, vol. 39, pp. 449-454.*
Oda et al, Development and evaluation of a practical ELISA for human urinary lipocalin-type prostaglandin D synthase.*
Melegos et al, Immunofluorometric assay of prostaglandin D synthase in human tissue extracts and fluids, 1996, Clinical Chemistry, vol. 42, pp. 1984-1991.*
Edelstam et al, New reference values for routine blood samples and human neutrophilic lipocalin during thrid-trimester pregnancy, 200, Scand J Clin Lab Invest, vol 61, pp. 583-591.*
Shiki et al.: "Changes of lipocalin-type prostaglandin D synthase level during pregnancy". J. Obstet. Gynaecol. Res., vol. 30, No. 1, pp. 65-70 (Feb. 2004).
Melegos et al.: "Prostaglandin D2 synthase: a component of human amniotic fluid and its association with fetal abnormalities". Clinical Chemistry, vol. 42, No. 7, pp. 1042-1050 (1996).
Shiki et al.: "Changes of lipocalin-type prostaglandin D synthase level during pregnancy". J. Obstet. Gynaecol. Res., vol. 30, No. 1, pp. 65-70 (Feb. 2004).
Melegos et al.: "Prostaglandin D2 synthase: a component of human amniotic fluid and its association with fetal abnormalities". Clinical Chemistry, vol. 42, No. 7, pp. 1042-1050 (1996).
English Language Abstract of JP2001-220354.
English Language Abstract of JP2001-215226.

* cited by examiner

*Primary Examiner*—Mark Navarro
(74) *Attorney, Agent, or Firm*—Greenblum & Bernstein, P.L.C.

(57) ABSTRACT

Provided are: a method for predicting the onset of pregnancy-induced hypertension (PIH) by precisely detecting abnormalities that occur before the onset of PIH (where such abnormalities have been impossible to detect by various conventional testing methods for PIH) while imposing less of a burden on a subject; a method for evaluating a fetus and placental functions in PIH; and a method for detecting PIH, which comprises measuring the level of human lipocalin-type prostaglandin D synthase (L-PGDS) in a body fluid sample collected from a subject.

6 Claims, 6 Drawing Sheets

METHOD FOR PREDICTING PREGNANCY-INDUCED HYPERTENSION

TECHNICAL FIELD

The present invention relates to a method for determining the severity of and predicting pregnancy-induced hypertension (PIH). Specifically, the present invention relates to a method for conveniently and objectively determining PIH and a method for predicting the risk of the onset of PIH in a pregnant woman who has not show any clinical symptoms of PIH. Furthermore, the present invention relates to a method for evaluating a fetus and placental functions in PIH.

BACKGROUND ART

Pregnancy-induced hypertension (PIH) is a major cause of death in pregnant and parturient women in addition to bleeding, obstetrical pulmonary embolus, and the like. A method for managing PIH is still an important issue for obstetricians. However, the cause and morbidity of PIH remain unknown. Furthermore, the definition and classification of PIH have not yet been unified worldwide. In Japan, PIH is defined by the presence of at least one of hypertension, proteinuria, and edema as symptoms during pregnancy, where these symptoms are not simple accidental complications of pregnancy. However, hypertension is absolutely the major symptom that indicates PIH. A case in which edema alone is exhibited is not said to be PIH. PIH is found in approximately 10% of pregnant women (6% to 14%).

PIH is classified into early onset type (onset before pregnancy week 32) and late onset type (onset at and after pregnancy week 32) depending on the onset timing. Classification of PIH in terms of severity is as follows. A case in which one or more of hypertension, proteinuria, and edema as symptoms are exhibited, which are all determined to be mild, is determined to constitute mild-type PIH. A case in which at least one of these symptoms, which is determined to be severe, is exhibited is determined to constitute severe-type PIH. In both early onset type and severe-type PIH, organ damage becomes rapidly worse in both the mother and the fetus, so that prognosis is bad. Thus, these types of PIH require strict management.

PIH is diagnosed by examining the symptoms of hypertension, proteinuria, and edema. Specifically, hypertension is determined to exist when systolic blood pressure is 140 mmHg or more and diastolic blood pressure is 90 mmHg or more. Furthermore, proteinuria is determined to exist when 30 mg/dL or more protein is detected in 24 hour urine specimen by Esbach's method or a measurement method according thereto. Edema is determined to exist when a tibial crest remains depressed after digital compression and body weight gain of 500 g or more is observed during the most recent 1 week of pregnancy. When at least one of these symptoms is observed, a diagnosis of PIH is made (edited by Shoichi Sakamoto, et al., Pregnancy-induced hypertension, Principles of Obstetrics and Gynecology 2: MEDICAL VIEW CO., LTD., 1998: 340-60).

Furthermore, a general PIH case leads to decreased circulating blood volume and is associated with hemoconcentration. Thus, plasma protein concentration may also be measured. Furthermore, severe PIH often leads to microthrombus formation that indicates an elevated state of the coagulation system and the same with respect to the secondary fibrinolytic system. Thus, factors involved in such coagulation-fibrinolytic system, such as blood platelets and D-dimer, are also examined. Furthermore, lipids, hepatic functions, and the like are also tested if necessary (edited by Shoichi Sakamoto et al., Pregnancy-induced hypertension. Principles of Obstetrics and Gynecology 2: MEDICAL VIEW CO., LTD. 1998: 340-60).

Management of a patient with PIH and therapeutic methods therefore vary depending on severity. However, the severity of PIH is currently determined comprehensively by a combination of the above-described plurality of testing methods. Therefore, establishment of a method for conveniently and objectively determining severity is desired. Moreover, it is thought that the influence of PIH can be substantially suppressed by strict management when PIH is found at the initial stage. However, detection of PIH at the initial stage is difficult via any of the above-described testing methods. Currently, no indicator for predicting the onset of PIH has been established.

Furthermore, when PIH becomes more severe, placental functions will decrease and the nutritional and oxygen conditions of a fetus will be worse. Determination of such functions is very important in determination of delivery timing for a fetus. Accordingly, a precise indicator for evaluating fetuses and placental functions is desired.

Human lipocalin-type prostaglandin D synthase (hereinafter, L-PGDS) is an enzyme that catalyzes isomerization from $PGH_2$, which is a common precursor of various prostaglandins, to $PGD_2$. L-PGDS is a multifunctional protein because it also has a function of transporting small hydrophobic molecules (Urade Y. et al., Prostaglandin D synthase: Structure and Function. Vitam Horm 2000; 58: 89-120). It has been reported that elevated blood L-PGDS levels(concentrations) are detected in patients with advanced renal disease (Hoffmann A. et al., Molecular Characterization of β-trace Protein in Human Serum and Urine: A Potential Diagnostic Marker for Renal Diseases. Glycobiology 1997; 7: 499-506). Furthermore, the present inventors have revealed that L-PGDS levels are increased in the body fluids of patients with early renal disease (before the progression of renal disease) (Hamano K. et al., Blood Sugar Control Reverses the Increase in Urinary Excretion of Prostaglandin D Synthase in Diabetic Patients. Nephron 2002; 92: 77-85). The present inventors have also revealed that L-PGDS is produced in atherosclerotic plaque and that L-PGDS levels are increased in the body fluids of patients with coronary artery disease (Eguchi Y. et al., Expression of Lipocalin-Type Prostaglandin D Synthase (β-trace) in Human Heart and its Accumulation in the Coronary Circulation of Angina Patients. Proc Natl Acad Sci U.S.A. 1997; 94: 14689-94). As described above, the relationship between L-PGDS and renal disease or vascular lesion has been revealed. However, the relationship between L-PGDS and PIH has net yet examined.

Non-patent document 1: Hoffmann A. et al., Glycobiology 1997; 7: 499-506

Non-patent document 2: Hamano K. et al., Nephron 2002; 92: 77-85

Non-patent document 3: Eguchi Y. et al., Proc Natl Acad Sci U.S.A. 1997; 94: 14689-94

DISCLOSURE OF THE INVENTION

An object of the present invention is to provide a method for conveniently and objectively determining the severity of PIH, which has been comprehensively determined by various testing methods. Another object of the present invention is to provide a method for predicting the onset of PIH by precisely detecting abnormalities that occur before the onset of PIH (such abnormalities have been impossible to detect by various conventional testing methods for PIH) while imposing less of a burden on a subject. Still another object of the present invention is to provide a method for evaluating a fetus and placental functions in PIH.

As a result of intensive studies to achieve the above objects, the present inventors have discovered that the severity of PIH can be determined by measuring L-PGDS levels in body fluids such as blood and urine and using the measured values as indexes. Furthermore, the present inventors have discovered that early prediction of PIH is possible with the use of such measured values as indexes. Thus, the present inventors have completed the research.

Specifically, the present invention relates to a method for determining the severity of or predicting PIH, which comprises measuring the level of L-PGDS in a body fluid sample collected from a subject.

Specifically, the present invention is as follows:

[1] a method for detecting pregnancy-induced hypertension, which comprises measuring the level of human lipocalin-type prostaglandin D synthase in a body fluid sample collected from a subject;

[2] the method for detecting pregnancy-induced hypertension according to [1], which comprises measuring the level of human lipocalin-type prostaglandin D synthase in a body fluid sample collected from a subject and comparing the measured value with a cut-off value that is determined based on measured values of human lipocalin-type prostaglandin D synthase in body fluid samples collected from normal pregnant women and/or pregnant women with pregnancy-induced hypertension;

[3] a method for determining the severity of pregnancy-induced hypertension, which comprises measuring the level of human lipocalin-type prostaglandin D synthase in a body fluid sample collected from a subject;

[4] the method for determining the severity of pregnancy-induced hypertension according to [3], which comprises measuring the level of human lipocalin-type prostaglandin D synthase in a body fluid sample collected from a subject and comparing the measured value with cut-off values that are determined according to the measured values of human lipocalin-type prostaglandin D synthase in the body fluid samples collected from pregnant women with various severities of pregnancy-induced hypertension;

[5] a method for predicting pregnancy-induced hypertension, which comprises measuring the level of human lipocalin-type prostaglandin D synthase in a body fluid sample collected from a subject;

[6] the method for predicting pregnancy-induced hypertension according to [5], which comprises measuring the level of human lipocalin-type prostaglandin D synthase in a body fluid sample collected from a subject showing no hypertension, proteinuria, or edema;

[7] the method for predicting pregnancy-induced hypertension according to [5] or [6], which comprises measuring the level of human lipocalin-type prostaglandin D synthase in a body fluid sample collected from a subject and comparing the measured value with a cut-off value that is determined from measured values of human lipocalin-type prostaglandin D synthase in body fluid samples collected from normal pregnant women and/or pregnant women with pregnancy-induced hypertension;

[8] a method for evaluating a fetus and a placental function, which comprises measuring the level of human lipocalin-type prostaglandin D synthase in a body fluid sample collected from a patient with pregnancy-induced hypertension;

[9] the method for detecting pregnancy-induced hypertension according to [1] or [2], wherein the level of human lipocalin-type prostaglandin D synthase in a body fluid sample is measured by an immunological assay method;

[10] the method for determining the severity of pregnancy-induced hypertension according to [3] or [4], wherein the level of human lipocalin-type prostaglandin D synthase in a body fluid sample is measured by an immunological assay method;

[11] the method for predicting pregnancy-induced hypertension according to any one of [5] to [7], wherein the level of human lipocalin-type prostaglandin D synthase in a body fluid sample is measured by an immunological assay method;

[12] the method for evaluating a fetus and a placental function according to [8], wherein the level of human lipocalin-type prostaglandin D synthase in a body fluid sample is measured by an immunological assay method;

[13] the method according to any one of [1] to [12], wherein the body fluid sample is blood;

[14] the method according to any one of [1] to [12], wherein the body fluid sample is urine; and

[15] a kit for detecting pregnancy-induced hypertension, which contains an anti-human lipocalin-type prostaglandin D synthase antibody.

The present invention will be explained in detail as follows.

This description includes part or all of the contents as disclosed in the description and/or drawings of Japanese Patent Application No. 2003-332084, which is a priority document of the present application.

BEST MODE OF CARRYING OUT THE INVENTION

Figure 1:
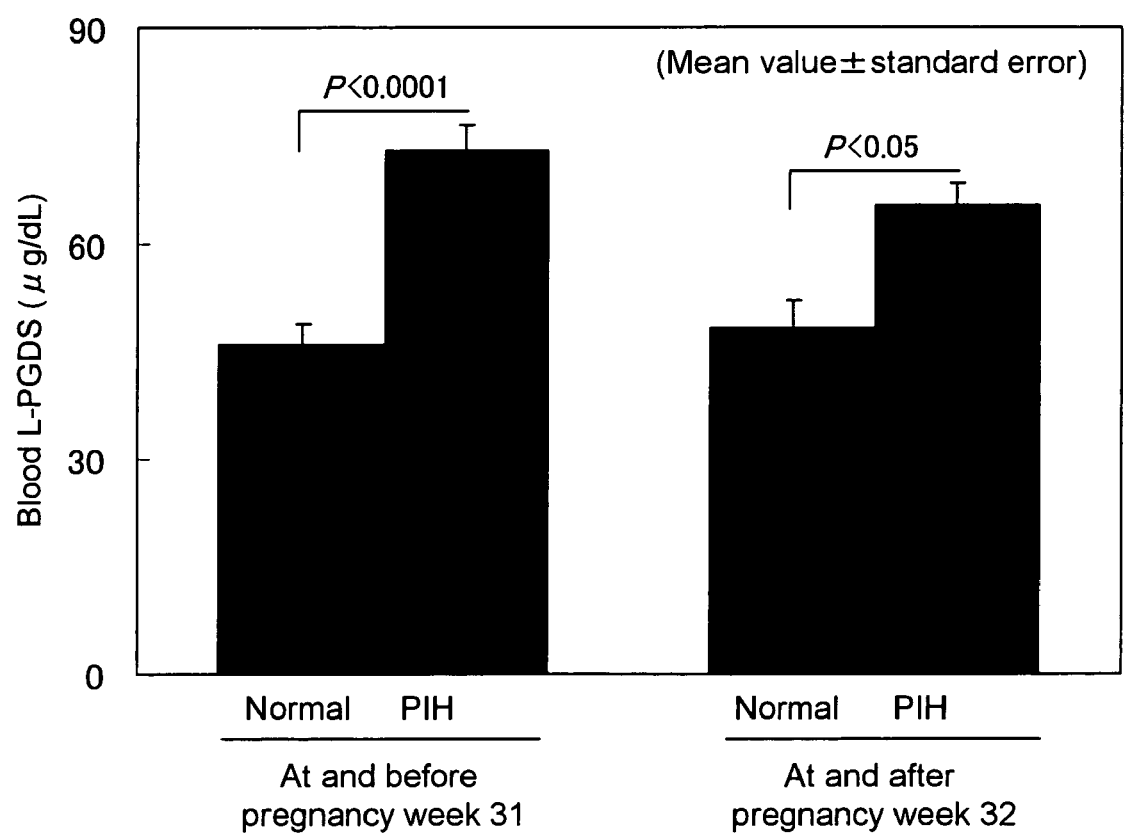
FIG. 1 shows blood L-PGDS levels in normal pregnant women and pregnant women with pregnancy-induced hypertension (PIH) at and before pregnancy week 31 and at and after pregnancy week 32. In all groups, blood L-PGDS levels were significantly higher in the subjects with PIH than in the normal subjects.

In the present invention, a sample containing L-PGDS to be measured is a body fluid collected from a subject. Specific examples of such sample include blood (e.g., serum or plasma), urine (e.g., spot urine specimens or timed urine specimens), amniotic fluids, cervical mucus, uterine luminal fluids, and oviduct luminal fluids. Of these examples, blood and urine are particularly preferable because they can be easily collected. In this case, a subject may be any pregnant woman regardless of her pregnancy stage (weeks that have passed after conception). Regarding a pregnant woman in the early stages of pregnancy, when PIH has not yet been developed, her future risk of developing PIH can be determined by the method of the present invention. Regarding a pregnant woman who has already shown symptoms of PIH, the severity of PIH can be determined by the method of the present invention. A method for measuring L-PGDS levels in the above samples is not particularly limited, as long as it can precisely reflect such L-PGDS levels. Examples of such method include an immunological assay method, an enzyme activity assay method, and a capillary electrophoresis method. However, in view of the necessity of simultaneously and conveniently measuring large amounts of samples at an actual clinical site, an immunological assay method using a monoclonal antibody or a polyclonal antibody specific to L-PGDS, such as an enzyme immunoassay method, a radioimmunoassay method, a latex agglutination assay method, or a fluorescence immunoassay method is preferable. A monoclonal antibody that can be preferably used herein is produced by a hybridoma strain 1B7 (FERM BP-5709), 7F5 (FERM BP-5711), 6F5 (FERM BP-5710), 9A6 (FERM BP-5712), 10A3 (FERM BP-5713), or the like. The hybridoma strain 1B7 was deposited on Sep. 21, 1995 (original deposition date) under FERM BP-5709, 7F5 was deposited on Jun. 6, 1996 (original deposition date) under FERM BP-5711, 6F5 was deposited on Sep. 21, 1995 (original deposition date) under FERM BP-5710, 9A6 was deposited on Jun. 6, 1996 (original deposition date) under FERM BP-5712, and 10A3 was deposited on Jun. 6, 1996 (original deposition date) under FERM BP-5713 with the International Patent Organism Depositary, National Institute of Advanced Industrial Science and Technology (Central 6, 1-1-1 Higashi, Tsukuba, Ibaraki, Japan). For example, an L-PGDS detection kit (WO97/16461) that the present inventors have already established as a kit to be used for a sandwich ELISA method using a monoclonal antibody may be used.

According to the present invention, PIH at the initial stage can be detected using an L-PGDS level measured by the above methods as an indicator. Furthermore, severe PIH can be predicted at an early stage. Furthermore, decreased placental functions in the case of PIH can be determined using an L-PGDS level measured by the above methods as an indicator.

PIH that is detected by the method of the present invention is limited to neither preeclampsia, gestational hypertension nor superimposed preeclampsia. Eclampsia associated with cerebral vasospasm seizure is also included. Moreover, PIH associated with HELLP (hemolysis, elevated liver enzymes, and low platelet count) syndrome, which induces pulmonary edema, encephalorrhagy, premature ablation of normally implanted placenta, or hepatic vasospasm is also included.

To determine by the method of the present invention whether or not a pregnant woman is affected with PIH, first a cut-off value is determined. For example, the levels of L-PGDS in body fluid samples collected from normal pregnant women and/or pregnant women who are already showing hypertension, proteinuria, or edema as a symptom and have been clinically diagnosed to have PIH are measured. Then, based on distribution of L-PGDS level in normal pregnant women or diagnostic accuracy, such as sensitivity and specificity in the detection of PIH, an appropriate cut-off value for L-PGDS is determined. Subsequently, the level of L-PGDS in a body fluid sample collected from a pregnant woman who is a subject is measured, followed by comparison of the measured value with the cut-off value. When the L-PGDS level in a subject is higher than the cut-off value, it can be determined that the subject is affected with PIH. Cut-off values may be previously determined according to various severities of PIH. Through comparison of a measured L-PGDS value in a subject with each of such cut-off values, the severity of PIH can be determined. For example, subjects with PIH are divided into a group of those with severe-type or a group of those with mild-type PIH based on clinical symptoms such as hypertension, proteinuria, and edema. Distribution of L-PGDS level in each group and diagnostic accuracy for determination of the severity are examined, so that appropriate cut-off values may be determined. The number of subjects for determination of the above cut-off values is not limited. The number of cases is preferably 5 or more and further preferably 10 or more.

According to the method of the present invention, PIH at the initial stage can also be determined, which is impossible to precisely determine based only on symptoms such as hypertension, proteinuria, and edema.

A cut-off value to be used in such case is not limited. Specifically, in the case of blood level, a cut-off value for determining whether or not a subject is affected with PIH can be determined to be between 50 and 70 µg/dL, for example, for a pregnant woman at and before pregnancy week 31 and can be determined to be between 50 and 60 µg/dL, for example, for a pregnant woman at and after pregnancy week 32. Moreover, in the case of urinary excretion (level), a cut-off value can be determined to be between 2.7 and 9 mg/g creatinine for a pregnant woman at and before pregnancy week 31, and can be determined to be between 3.5 and 7.5 mg/g creatinine for a pregnant woman at and after pregnancy week 32. Furthermore, a cut-off value for determining if PIH is mild-type or severe-type is also not limited. For example, in the case of blood level, such a cut-off value can be determined to be between 55 and 70 µg/dL. In the case of urinary excretion, such a cut-off value can be determined to be between 4 and 9 mg/g creatinine. When a measured L-PGDS value in a subject is higher than a cut-off value used for determining whether or not a subject is affected with PIH and is lower than a cut-off value used for determining if PIH is mild-type or severe-type, it is determined that the relevant subject is affected with mild-type PIH. When a measured value is higher than a cut-off value used for determining if PIH is mild-type or severe-type, it is determined that the relevant subject is affected with severe-type PIH.

Moreover, the method of the present invention also encompasses a method for determining a risk of developing PIH in the pregnant woman who shows none of hypertension, proteinuria, and edema as symptoms and thus is thought not to be clinically affected with PIH, that is, a method for predicting PIH. In this case, L-PGDS levels in body fluid samples collected from normal pregnant women are measured. Subsequently, the conditions of pregnancy of the normal pregnant women are prospectively observed. Such subject pregnant women are divided into a group of pregnant women who have delivered their babies without developing PIH and a group of pregnant women who have developed PIH during pregnancy. A cut-off value for prediction is determined to be between the measured L-PGDS values of the former group and the measured L-PGDS values of the latter group. Alternatively, body fluid samples are collected from pregnant women with PIH before the onset of PIH. Body fluid samples are also collected from pregnant women who have delivered their babies without developing PIH. All of these samples are collected during the similar pregnancy period. These samples are stored by means such as freezing. Through measurement of L-PGDS levels in such stored samples, a cut-off value can also be determined retrospectively. Moreover, pregnant women are divided by the onset timing of PIH. L-PGDS levels are measured for each group of pregnant women and then a cut-off value can be determined for each onset timing. Thus, the onset timing of PIH can also be predicted. For example, pregnant women are divided into a group of pregnant women who have developed PIH in the early stage of pregnancy (pregnancy weeks 15 to 25) and a group of pregnant women who have developed PIH in the late stage of pregnancy (at and after pregnancy week 26). Through measurement of L-PGDS levels in body fluid samples of each group, it becomes possible to determine the risk of developing PIH in the early stage of pregnancy and the risk of developing PIH in the late stage of pregnancy. Furthermore, pregnant women are divided into a group of pregnant women who have developed mild-type PIH and a group of pregnant women who have developed severe-type PIH. L-PGDS levels in the body fluid samples of each group are measured. A cut-off value is then determined between L-PGDS levels (measured before the onset) of pregnant women who have developed severe-type PIH and L-PGDS levels (measured before onset) of pregnant women who have developed mild-type PIH. Hence, the risk of developing severe-type PIH can be determined.

Subsequently, a body fluid sample is collected from a pregnant woman showing none of hypertension, proteinuria, and edema as symptoms and then the L-PGDS level is measured. The measured L-PGDS value is compared with the above cut-off value for prediction. Thus, the risk of developing PIH is determined. For example, when a measured value is higher than such a cut-off value, it is determined that the risk of developing PIH in the future is high. When the same is lower than such a cut-off value, it is determined that the risk of developing PIH in the future is low. Furthermore, when there is no difference between a measured value and such a cut-off value, determination is suspended. Reexamination may be performed if necessary.

A cut-off value in this case is not limited. For example, a cut-off value for predicting whether or not a subject develops PIH during pregnancy can be determined to be between 55 and 75 μg/dL in the case of blood level, and between 3.0 and 10 mg/g creatinine in the case of urinary excretion. Moreover, a cut-off value for predicting whether or not a subject develops severe-type PIH during pregnancy can be determined to be between 60 and 75 μg/dL in the case of blood level and between 5.0 and 10 mg/g creatinine in the case of urinary excretion.

As described above, the risk of developing PIH is determined. When such risk is determined to be high, the relevant pregnant woman is appropriately treated, so that the risk of developing PIH later or the risk of developing more severe PIH can be reduced. The number of subjects needed for determination of the above cut-off value is not limited. The number of cases is preferably 5 or more and further preferably 10 or more.

Furthermore, the present invention encompasses a method for evaluating a fetus and placental functions, which comprises measuring the level of L-PGDS in a body fluid sample collected from a pregnant woman who has developed PIH. Here, the term "evaluation of a fetus and placental functions" means evaluation of whether or not placental functions for supplying nutrition and oxygen to a fetus decrease or means to evaluate whether or not any injury such as organ damage occurs in the fetus. When the L-PGDS level in a body fluid sample is low, the fetus and placental functions are evaluated to be in a good state. When the same is high, the fetus and placental functions are evaluated to be in a sub-optimal state.

Furthermore, the present invention encompasses a reagent for detecting or a kit for detecting PIH, which comprises an anti-L-PGDS antibody. The reagent or the kit may contain a carrier to which an antibody is immobilized when such kit is based on an enzyme immunoassay method. Such an antibody may be previously bound to a carrier. Furthermore, the kit may also appropriately contain a blocking solution, a reaction solution, a stop solution, a reagent for treating a sample, instructions containing each cut-off value listed therein, a standard reagent wherein the L-PGDS level is prepared to be the same as a cut-off value, and the like.

The present invention will be described in detail by examples as follows, but the scope of the present invention is not limited by these examples.

REFERENCE EXAMPLE

Method for Measuring L-PGDS Level in Body Fluid

The L-PGDS level in a body fluid was measured by the sandwich ELISA method as follows.

First, an anti-human L-PGDS monoclonal antibody (clone: 7F5) capable of binding to human L-PGDS was diluted with a 50 mM carbonate buffer (pH 9.6) to a level of 4.4 μg/mL. The solution was added at 300 μL/well to a 96-well microtiter plate and then incubation was performed at 4° C. overnight for immobilization. The plate was washed 3 times with phosphate buffered saline (pH 7.4; hereinafter, PBS). Blocking was performed by adding PBS containing 0.2% casein (pH 7.4; hereinafter, a blocking solution) at 300 μL/well and then performing incubation at 30° C. for 90 minutes. Subsequently, the plate obtained after blocking was washed 3 times with PBS containing 0.05% Tween20 (T-PBS). An antigen solution (a standard solution or a body fluid specimen diluted with a blocking solution) was added to the plate at 100 μL/well, followed by incubation at 30° C. for 90 minutes. After reaction, the plate was washed 3 times with T-PBS. A horseradish-peroxidase-labeled anti-human L-PGDS monoclonal antibody (clone: 1B7) was diluted with a blocking solution to a concentration of 0.5 μg/mL. The diluted solution was then added at 100 μL/well to the plate and then incubation was performed at 30° C. for 90 minutes. After reaction, the plate was washed 3 times with T-PBS. A coloring solution (ABTS solution: produced by Boehringer Mannheim Corporation) was added at 100 μL/well, followed by incubation at 30° C. for 30 minutes. After reaction, a stop solution (1.5% oxalic acid) was added at 100 μL/well and then each solution was stirred with a plate mixer, so as to stop the reaction. Absorbance was determined at 405 nm using a commercial plate reader.

The monoclonal antibodies (clones: 1B7 and 7F5) used in the above sandwich ELISA method were prepared as follows. 1.0 mL of pristane was injected intraperitoneally into each mouse. 2 weeks after injection, $1 \times 10^8$ hybridoma cells producing the 1B7 or 7F5 antibody were transplanted intraperitoneally into each mouse. An ascites fluid was collected 2 weeks later and then the obtained ascites fluid was subjected to protein A affinity column chromatography operation. In addition, each cell line producing the above monoclonal antibody agrees with each monoclonal antibody name. Furthermore, the 1B7 cell line and the 7F5 cell line were deposited with the International Patent Organism Depositary, National Institute of Advanced Industrial Science and Technology (Central 6, 1-1-1 Higashi, Tsukuba, Ibaraki, Japan) under FERM BP-5709 (original deposition date: Sep. 21, 1995) and under FERM BP-5711 (original deposition date: Jun. 6, 1996), respectively.

EXAMPLE 1

Blood L-PGDS levels of normal pregnant women and pregnant women with PIH were measured. Subjects were divided into subjects at and before pregnancy week 31 and subjects at and after pregnancy week 32 depending on pregnancy stages. The blood L-PGDS levels of the normal pregnant women were compared with those of the pregnant women with PIH at each stage. FIG. 1 shows the results. Regarding the subjects at and before pregnancy week 31, the L-PGDS level was significantly higher (P<0.0001) in the PIH group (n=10, 72.8±3.8 μg/dL, mean value±standard error) than that in the normal group (n=14, 46.1 ±2.8 μg/dL, mean value±standard error). Moreover, regarding the subjects at and after pregnancy week 32, the L-PGDS level was also significantly higher (P<0.05) in the PIH group (n=10, 65.4±3.1 μg/dL, mean value±standard error) than that in the normal group (n=13, 48.3±3.8 μg/dL, mean value±standard error). Hence, it was concluded that at any pregnancy stage, a subject showing a high blood L-PGDS level is likely to develop PIH and that measurement of blood L-PGDS level is useful for detection of PIH.

EXAMPLE 2

Figure 2:
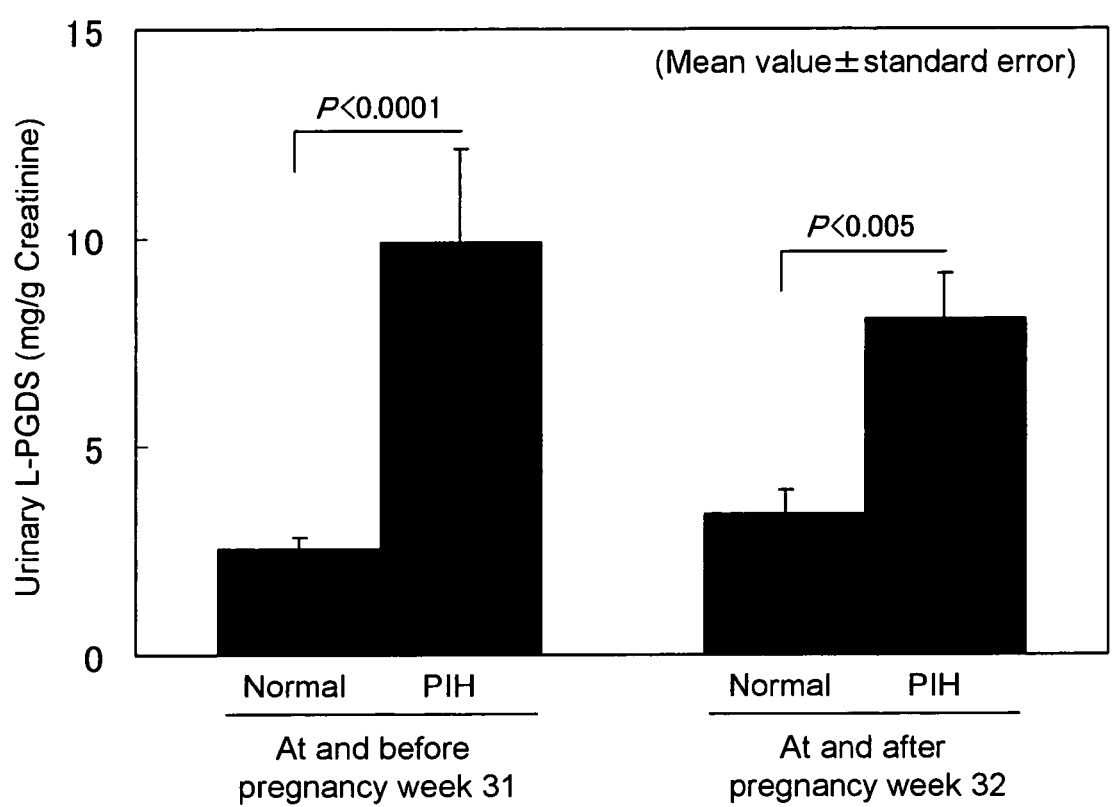
FIG. 2 shows the urinary L-PGDS excretions (levels) in normal pregnant women and pregnant women with PIH at and before pregnancy week 31 and at and after pregnancy week 32. Spot urine was used as specimen. Each measured L-PGDS value was divided by the urinary creatinine level (L-PGDS per gram of creatinine). In all groups, urinary L-PGDS excretions were significantly higher in the subjects with PIH than in the normal subjects.

The levels of L-PGDS excreted into an urine of normal pregnant women and pregnant women with PIH were measured. Subjects were divided into subjects at and before pregnancy week 31 and subjects at and after pregnancy week 32 depending on pregnancy stages. Spot urine specimens from the normal pregnant women and the pregnant women with PIH at each stage were collected. To correct for an influence of the urine volume, each urinary L-PGDS value was divided by urinary creatinine (L-PGDS/g creatinine). FIG. 2 shows the results. Regarding the subjects at and before pregnancy week 31, the L-PGDS excretion was significantly higher (P<0.0001) in the PIH group (n=10, 9.90±2.24 mg/g creatinine, mean value±standard error) than that in the normal group (n=14, 2.53±0.26 mg/g creatinine, mean value±standard error). Moreover, regarding the subjects at and after pregnancy week 32, the L-PGDS excretion was also significantly higher (P<0.005) in the PIH group (n=10, 8.03±1.11 mg/g creatinine, mean value±standard error) than that in the normal group (n=14, 3.38±0.58 mg/g creatinine, mean value±standard error). Hence, it was concluded that at any pregnancy stage, a subject showing a high urinary L-PGDS excretion is likely to develop PIH and that measurement of urinary L-PGDS excretion is useful for detection of PIH.

EXAMPLE 3

Figure 3:
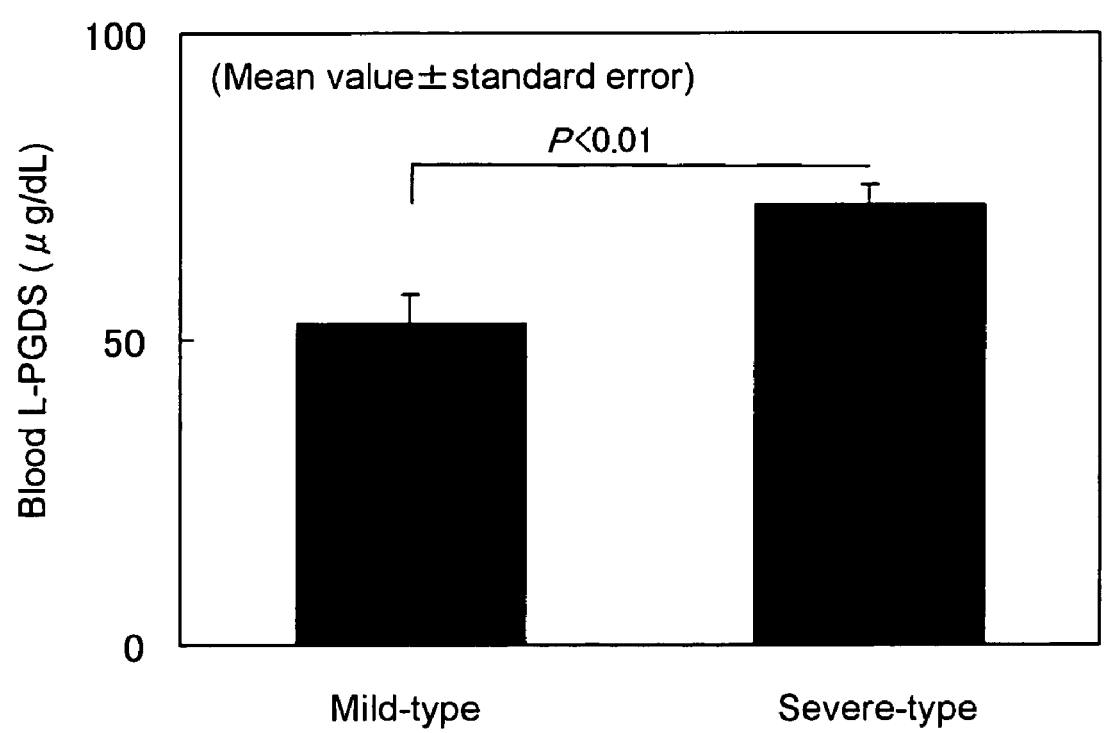
FIG. 3 shows the results of comparing blood L-PGDS levels in the pregnant women with mild-type and severe-type PIH at pregnancy weeks 26 to 38. Severity of PIH was determined by clinical symptoms and the like. Blood L-PGDS levels were significantly higher in the case of severe-type PIH than those in the case of mild-type PIH.

Blood L-PGDS levels of pregnant women with PIH at pregnancy weeks 26 to 38 were measured. Subjects were divided into subjects with mild-type PIH and subjects with severe-type PIH based on hypertension, proteinuria, edema, other clinical symptoms, and the like. The blood L-PGDS levels thereof were compared. As a result, as shown in FIG. 3, the blood L-PGDS level was significantly higher (P<0.01) in severe-type group (n=12, 71.9±3.6 μg/dL, mean value±standard error) than that in mild-type group (n=9, 52.4±4.8 μg/dL, mean value±standard error). Hence, it was concluded that PIH is likely to be severe when a patient with PIH shows a high blood L-PGDS level and that measurement of blood L-PGDS level is useful in determination of the severity of PIH.

EXAMPLE 4

Figure 4:
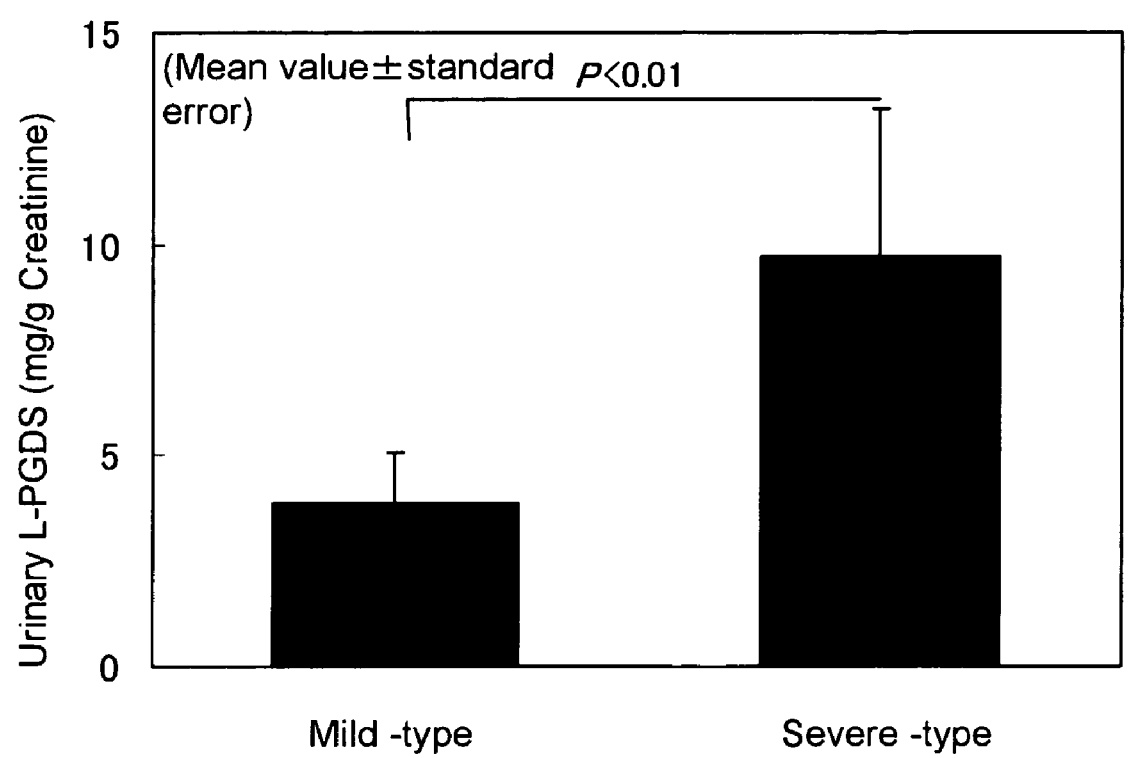
FIG. 4 shows the results of comparing urinary L-PGDS excretions in the pregnant women with mild-type and severe-type PIH at pregnancy weeks 26 to 38. Severity of PIH was determined by clinical symptoms and the like. Urinary L-PGDS excretions were significantly higher in the case of severe-type PIH than those in the case of mild-type PIH.

The levels of L-PGDS excreted into an urine of pregnant women with PIH at pregnancy weeks 26 to 38 were measured. Subjects were divided into subjects with mild-type PIH and subjects with severe-type PIH based on hypertension, proteinuria, edema, other clinical symptoms, and the like. The urinary L-PGDS excretions thereof were compared. Spot urine was used as specimen. Each urinary L-PGDS value was divided by the urinary creatinine concentration (L-PGDS per gram of creatinine). As a result, as shown in FIG. 4, the urinary L-PGDS excretion was significantly higher (P<0.01) in severe-type group (n=12, 9.72±3.46 mg/g creatinine, mean value±standard error) than that in mild-type group (n=9, 3.87±1.18 mg/g creatinine, mean value±standard error). Hence, it was concluded that PIH is likely to be severe when a patient with PIH shows a high urinary L-PGDS excretion and that measurement of urinary L-PGDS excretion is useful in determination of the severity of PIH.

EXAMPLE 5

Blood L-PGDS levels of 24 pregnant women at pregnancy weeks 15 to 25, who had not developed PIH, were measured. During the period from the L-PGDS measurement to delivery, the subjects were prospectively observed to determine the presence or the absence of the onset of PIH. The presence or the absence of the onset of PIH was determined comprehensively based on hypertension, proteinuria, edema, other clinical symptoms, and the like. A provisional cut-off value was set at 61.8 μg/dL, which was the 95 percentile of blood L-PGDS levels in normal pregnant women at and before pregnancy week 31 as shown in Example 1. The subjects were classified into a group of subjects showing L-PGDS levels equal to or lower than the cut-off value and a group of subjects showing L-PGDS levels higher than the cut-off value. As a result, as shown in Table 1, whereas only 1 out of 17 subjects developed PIH (5.9%) in the group of subjects showing blood L-PGDS levels equal to or lower than 61.8 μg/dL, 2 out of 7 subjects developed PIH (as high as 28.6%) in the group of subjects showing L-PGDS levels higher than 61.8 μg/dL. Based on this result, it was concluded that even in the case of a pregnant woman who has not developed PIH, such a subject is likely to develop PIH when her blood L-PGDS level is high. It was also concluded that the onset of PIH can be predicted by measuring blood L-PGDS level.

TABLE 1

Blood L-PGDS level and the following onset of PIH

| Case No. | Blood L-PGDS (μg/dL) | Onset of PIH |
|---|---|---|
| 1 | 40 | No |
| 2 | 64.6 | Yes |
| 3 | 51.1 | No |
| 4 | 38.6 | No |
| 5 | 39.0 | No |
| 6 | 37.8 | No |
| 7 | 59.5 | Yes |
| 8 | 58.8 | No |
| 9 | 49.5 | No |
| 10 | 76.0 | No |
| 11 | 39.8 | No |
| 12 | 53.5 | No |
| 13 | 64.8 | No |
| 14 | 46.8 | No |
| 15 | 50.5 | No |
| 16 | 68.2 | No |
| 17 | 43.0 | No |
| 18 | 48.7 | No |
| 19 | 34.6 | No |
| 20 | 62.3 | No |
| 21 | 44.8 | No |
| 22 | 59.6 | No |
| 23 | 64.3 | No |
| 24 | 78.8 | Yes |

L-PGDS > 61.8 μg/dL

EXAMPLE 6

The levels of L-PGDS excreted into an urine of 35 pregnant women at weeks 15 to 25, who had not developed PIH, were measured. During the period from the L-PGDS measurement to delivery, the subjects were prospectively observed to determine the presence or the absence of the onset of PIH. The presence or the absence of the of the onset of PIH was determined comprehensively based on hypertension, proteinuria, edema, other clinical symptoms, and the like. Spot urine was used as specimen. Each urinary L-PGDS value was divided by the urinary creatinine concentration (L-PGDS per gram of creatinine). A provisional cut-off value was set at 4.21 mg/g creatinine, which was the 95 percentile of urinary L-PGDS excretions in normal pregnant women at and before pregnancy week 31 as shown in Example 2. The subjects were classified into a group of subjects showing L-PGDS excretions equal to or lower than the cut-off value and a group of subjects showing L-PGDS excretions higher than the cut-off value. As a result, as shown in Table 2, whereas only 2 out of 26 subjects developed PIH (7.7%) in the group of subjects showing urinary L-PGDS excretions equal to or lower than 4.21 mg/g creatinine, 3 out of 9 subjects developed PIH (as high as 33.3%) in the group of subjects showing L-PGDS excretions higher than 4.21 mg/g creatinine. Based on this result, it was concluded that even in the case of a pregnant woman who has not developed PIH, such a subject is likely to develop PIH when her urinary L-PGDS excretion is high. It was also concluded that the onset of PIH can be predicted by measuring urinary L-PGDS excretion.

TABLE 2

Urinary L-PGDS excretion and the following onset of PIH

| Case No. | Urinary L-PGDS (mg/g Creatinine) | Onset of PIH |
|---|---|---|
| 1 | 0.96 | No |
| 2 | 1.45 | No |
| 3 | 11.21 | Yes |
| 4 | 6.63 | No |
| 5 | 3.72 | No |
| 6 | 4.51 | No |
| 7 | 0.97 | No |
| 8 | 2.40 | No |
| 9 | 1.46 | No |
| 10 | 2.91 | Yes |
| 11 | 1.90 | No |
| 12 | 1.12 | No |
| 13 | 0.27 | No |
| 14 | 1.01 | No |
| 15 | 1.05 | No |
| 16 | 4.41 | No |
| 17 | 3.89 | No |
| 18 | 4.50 | Yes |
| 19 | 1.61 | No |
| 20 | 1.61 | No |
| 21 | 1.57 | No |
| 22 | 2.94 | No |
| 23 | 2.26 | No |
| 24 | 2.06 | No |
| 25 | 3.72 | No |
| 26 | 0.13 | No |
| 27 | 0.80 | No |
| 28 | 4.75 | No |
| 29 | 1.80 | No |
| 30 | 4.17 | Yes |
| 31 | 4.78 | No |
| 32 | 6.69 | No |
| 33 | 3.49 | No |
| 34 | 2.16 | No |
| 35 | 12.98 | Yes |

L-PGDS > 4.21 mg/g Creatinine

EXAMPLE 7

Figure 5:
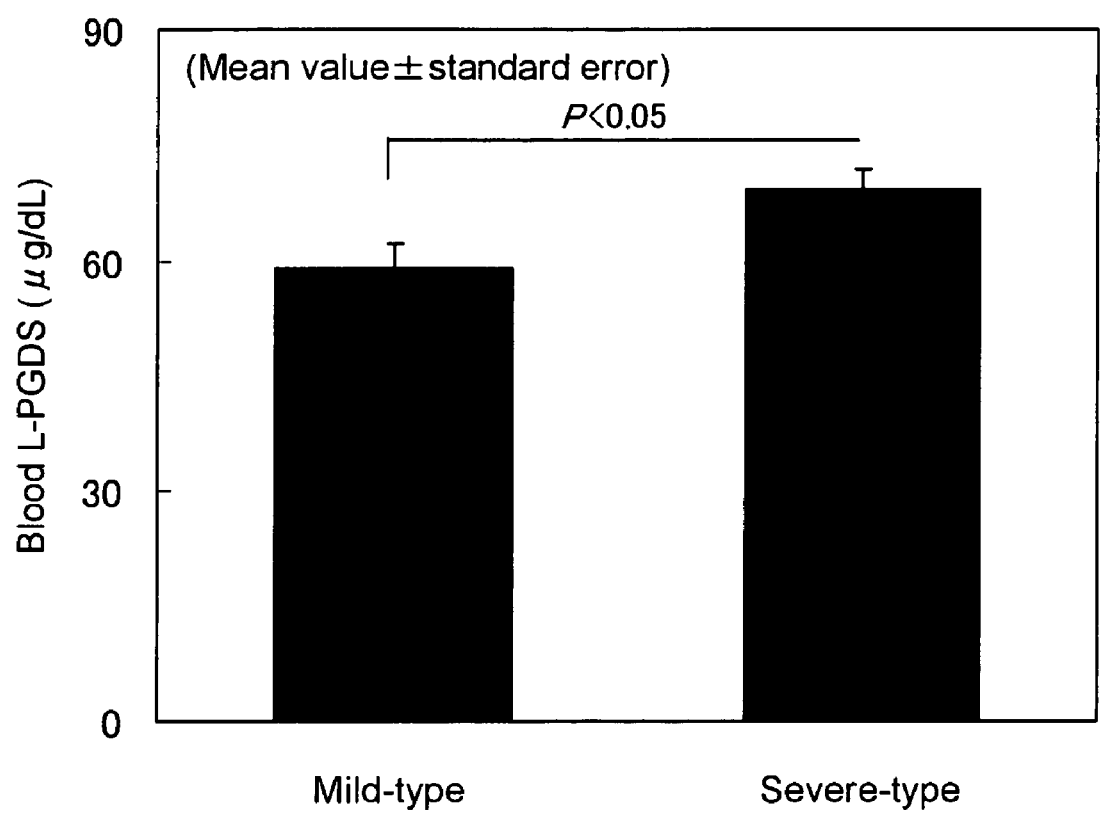
FIG. 5 shows the results of measuring L-PGDS levels in conserved sera collected from pregnant women before the onset of PIH. The subject pregnant women were determined to have mild-type or severe-type PIH based on clinical symptoms and the like. L-PGDS levels were significantly higher in the case of severe-type PIH than those in the case of mild-type PIH.

L-PGDS levels in conserved sera collected (during pregnancy weeks 15 to 25) from 17 pregnant women who had developed PIH at and after pregnancy week 26 were measured. As a result, as shown in FIG. 5, it was revealed that the L-PGDS level was significantly higher (P<0.05) in the case of severe-type PIH (n=8, 69.2±2.6 μg/dL, mean value±standard error) than that in the case of mild-type PIH (n=9, 58.9±3.2 μg/dL, mean value±standard error). Hence, it was concluded that a patient showing a high blood L-PGDS level is likely to develop severe-type PIH and that measurement of blood L-PGDS level is useful in prediction of severe-type PIH.

EXAMPLE 8

Figure 6:
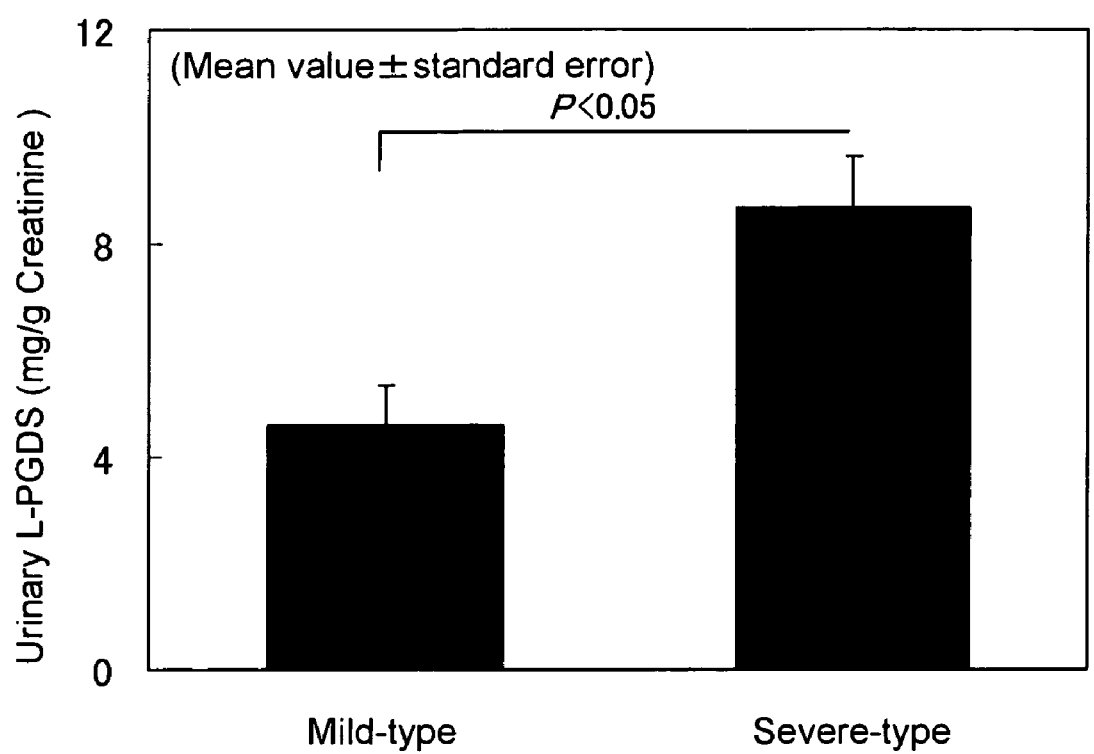
FIG. 6 shows the results of measuring urinary L-PGDS excretions in conserved urine collected from pregnant women before the onset of PIH. The subject pregnant women were determined to have mild-type or severe-type PIH based on clinical symptoms and the like. Spot urine was used as specimen. Each measured L-PGDS level was divided by the urinary creatinine concentration (L-PGDS per gram of creatinine). Urinary L-PGDS excretions were significantly higher in the case of severe-type PIH than those in the case of mild-type PIH.

L-PGDS excretions in conserved spot urine collected (during pregnancy weeks 15 to 25) from 17 pregnant women who had developed PIH at and after pregnancy week 26 were measured. As a result, as shown in FIG. 6, it was revealed that the L-PGDS excretion was significantly higher (P<0.05) in the case of severe-type PIH (n=8, 8.69±0.96 mg/g creatinine, mean value±standard error) than that in the case of mild-type PIH (n=8, 4.59±0.75 mg/g creatinine, mean value±standard error). Hence, it was concluded that a patient showing a high urinary L-PGDS excretion is likely to develop severe-type PIH and that measurement of urinary L-PGDS excretion is useful in prediction of severe-type PIH.

INDUSTRIAL APPLICABILITY

According to the present invention, a method by which PIH can be detected conveniently while imposing less of a burden on a subject is provided. Furthermore, by the use of the method of the present invention, the severity of PIH (that has been determined comprehensively using various testing methods) can be conveniently and objectively determined. Furthermore, by the use of the method of the present invention, the risk of developing PIH in a pregnant woman who has not shown clinical symptoms such as hypertension, proteinuria, or edema can also be predicted. Therefore, the method of the present invention is extremely useful for determining the severity of and predicting PIH.

All publications, patents, and patent applications cited herein are incorporated herein by reference in their entirety.

The invention claimed is:

1. A method for predicting pregnancy-induced hypertension, which comprises measuring the level of human lipocalin-type prostaglandin D synthase in a body fluid sample collected from a subject and comparing the measured value with a cut-off value that is determined from measured values of human lipocalin-type prostaglandin D synthase in body fluid samples collected from normal pregnant women not exhibiting symptoms of hypertension, proteinuria, and edema and not thought to be clinically affected with PIH and/or pregnant women with pregnancy-induced hypertension, wherein it is determined that the risk of developing PIH in the future is high when the measured value of human lipocalin-type prostaglandin D synthase is higher than the cut-off value.

2. The method for predicting pregnancy-induced hypertension according to claim 1, wherein the level of human lipocalin-type prostaglandin D synthase in a body fluid sample is measured by an immunological assay method selected from the group consisting of an enzyme immunoassay method, a radio-immunoassay method, a latex agglutination assay method, and a fluorescence immunoassay method.

3. The method according to claim 1, wherein the body fluid sample is blood.

4. The method according to claim 1, wherein the body fluid sample is urine.

5. The method according to claim 2, wherein the body fluid sample is blood.

6. The method according to claim 2, wherein the body fluid sample is urine.

* * * * *

UNITED STATES PATENT AND TRADEMARK OFFICE
CERTIFICATE OF CORRECTION

PATENT NO. : 7,399,596 B2
APPLICATION NO. : 10/573072
DATED : July 15, 2008
INVENTOR(S) : Hiroshi Oda et al.

It is certified that error appears in the above-identified patent and that said Letters Patent is hereby corrected as shown below:

Title Page, Item (73) Assignees:
"Maruha Corporation, Tokyo (JP); Osaka Bioscience Institute, Suita-shi (JP)" should be --Maruha Nichiro Seafoods, Inc., Tokyo (JP); Osaka Bioscience Institute, Suita-shi (JP)--.

Title Page, Item (56) Ref. Cited:
Foreign Pat. Docs. delete "2004-220354" and insert --2001-220354--.

Signed and Sealed this

Twenty-fourth Day of February, 2009

JOHN DOLL
*Acting Director of the United States Patent and Trademark Office*